(12) United States Patent
Bedrio

(10) Patent No.: US 10,088,397 B2
(45) Date of Patent: Oct. 2, 2018

(54) FLUID SEPARATOR COLLECTION CARD ASSEMBLY

(71) Applicant: Advance Dx, Inc., Scottsdale, AZ (US)

(72) Inventor: Ned Bedrio, Scottsdale, AZ (US)

(73) Assignee: Advance Dx, Inc., Scottsdale, AZ (US)

( * ) Notice: Subject to any disclaimer, the term of this patent is extended or adjusted under 35 U.S.C. 154(b) by 1258 days.

(21) Appl. No.: 13/921,934

(22) Filed: Jun. 19, 2013

(65) Prior Publication Data

US 2014/0373645 A1 Dec. 25, 2014

(51) Int. Cl.
  *G01N 37/00* (2006.01)
  *G01N 1/34* (2006.01)
  *B01L 3/00* (2006.01)
  *B01L 9/00* (2006.01)
  *G01N 1/00* (2006.01)

(52) U.S. Cl.
  CPC .............. *G01N 1/34* (2013.01); *B01L 3/5023* (2013.01); *B01L 9/52* (2013.01); *B01L 2200/185* (2013.01); *B01L 2300/045* (2013.01); *B01L 2300/048* (2013.01); *B01L 2300/0609* (2013.01); *B01L 2300/069* (2013.01); *B01L 2300/0825* (2013.01); *B01L 2400/0406* (2013.01); *G01N 2001/005* (2013.01)

(58) Field of Classification Search
  CPC ....... G01N 1/00; G01N 1/28; B01L 2200/141
  USPC ...................................................... 73/864.91
  See application file for complete search history.

(56) References Cited

U.S. PATENT DOCUMENTS

| 4,055,394 A | 10/1977 | Friedman et al. |
| 4,673,657 A * | 6/1987 | Christian ............. B01J 19/0093 422/301 |
| 4,678,757 A | 7/1987 | Rapkin et al. |
| 4,933,092 A | 6/1990 | Aunet et al. |
| 4,943,522 A | 7/1990 | Eisinger et al. |
| 4,999,285 A | 3/1991 | Stiso |
| 5,064,541 A | 11/1991 | Jeng et al. |
| 5,147,780 A * | 9/1992 | Pouletty ................ C23C 16/487 422/504 |

(Continued)

FOREIGN PATENT DOCUMENTS

| DE | 4341005 | 6/1995 |
| EP | 0183442 | 6/1986 |

(Continued)

OTHER PUBLICATIONS

International Search Report of PCT/US08/63707 dated Aug. 7, 2008 (2 pages).

(Continued)

*Primary Examiner* — Peter Macchiarolo
*Assistant Examiner* — Rodney T Frank
(74) *Attorney, Agent, or Firm* — Maginot, Moore & Beck, LLP

(57) ABSTRACT

A fluid sample collection card assembly in one embodiment includes a case including a tray assembly receiving cavity accessible through a mouth portion of the case, and a tray assembly, the tray assembly including an absorbent layer supported by a base portion, the base portion including (i) a tray portion configured to be removably received within the tray assembly receiving cavity and (ii) a faceplate portion configured to at least substantially close the mouth when the tray portion is received within the tray assembly receiving cavity.

13 Claims, 3 Drawing Sheets

(56) References Cited

U.S. PATENT DOCUMENTS

| | | | |
|---|---|---|---|
| 5,208,163 | A | 5/1993 | Charlton et al. |
| 5,409,664 | A | 4/1995 | Allen |
| 5,435,970 | A | 7/1995 | Mamenta et al. |
| 5,547,873 | A | 8/1996 | Magneson et al. |
| 5,589,399 | A | 12/1996 | Allen et al. |
| 5,866,007 | A | 2/1999 | Whitson et al. |
| 5,916,521 | A | 6/1999 | Bunce et al. |
| 6,258,045 | B1 | 7/2001 | Ray et al. |
| 6,316,205 | B1 | 11/2001 | Guan et al. |
| 6,357,583 | B1 | 3/2002 | Rainen |
| 6,365,417 | B1 | 4/2002 | Fleming et al. |
| 6,465,202 | B1 | 10/2002 | Tyrrell |
| 6,524,533 | B1 | 2/2003 | Tyrrell |
| 7,115,421 | B2 | 10/2006 | Grzeda et al. |
| RE39,664 | E | 5/2007 | Gordon et al. |
| 7,268,179 | B2 | 9/2007 | Brown |
| D560,811 | S | 1/2008 | Powell et al. |
| 7,838,258 | B2 | 11/2010 | Yang et al. |
| 7,867,780 | B2 | 1/2011 | Jones et al. |
| 8,062,608 | B2 | 11/2011 | Pankow |
| 2002/0192835 | A1 | 12/2002 | Cho et al. |
| 2003/0045814 | A1* | 3/2003 | Sangha ............... A61B 10/0051 600/573 |
| 2004/0023399 | A1 | 2/2004 | Grzeda et al. |
| 2006/0115805 | A1 | 6/2006 | Hansen et al. |
| 2006/0271017 | A1* | 11/2006 | Booth ................ A61B 19/0271 604/540 |
| 2007/0048345 | A1 | 3/2007 | Huang et al. |
| 2008/0210644 | A1 | 9/2008 | Milunic et al. |
| 2009/0117660 | A1 | 5/2009 | Dai et al. |
| 2010/0274155 | A1* | 10/2010 | Battrell ............. B01L 3/502715 600/572 |
| 2011/0318404 | A1* | 12/2011 | Kushnir .................. A61L 15/40 424/445 |
| 2012/0282634 | A1 | 11/2012 | Hughes et al. |

FOREIGN PATENT DOCUMENTS

| | | |
|---|---|---|
| EP | 0806666 | 11/1997 |
| EP | 1387170 | 2/2004 |
| WO | 9641817 A1 | 12/1996 |
| WO | 0136974 | 5/2001 |
| WO | 2006083053 | 8/2006 |

OTHER PUBLICATIONS

European Search Report in corresponding European patent application (i.e., EP 08 75 5539), dated Jul. 7, 2010 (6 pages).

European International Search Report corresponding to European Appl. No. PCT/US2014/034928 dated Aug. 25, 2014. (11 pages).

* cited by examiner

FLUID SEPARATOR COLLECTION CARD ASSEMBLY

FIELD OF THE INVENTION

The present invention relates to collection and separation of biological fluids. More particularly the invention relates to fluid sample collection devices used for collection and separation of fluids such as blood.

BACKGROUND

Biological samples are frequently used in laboratory and clinical settings to analyze various components in the samples. The biological samples include blood samples, sputum samples, and urine samples. Such samples, for example, are used to determine the levels or concentrations of various components such as HDL, LDL, Cholesterol, hemoglobin, detection of genes using DNA or RNA along with detection of HIV antibodies, or concentrations of drugs.

The biological sample is frequently processed in a liquid form. Accordingly, the liquid sample is collected, handled by the collection facility, transported to a laboratory, and stored pending processing. Activities surrounding a liquid blood sample present various problems including the risk of container breakage or leakage which causes loss of sample and the danger of infection, sample instability during shipment and storage, transport carrier restrictions related to transport of liquid biohazard materials, and collection of significantly more sample than is necessary for testing so as to ensure sufficient sample quantity is available for common methods of serum or plasma preparation and subsequent analysis. Thus, collection of several vials of fluid such as blood from a patient is not uncommon.

In response to the shortcomings of liquid sample collection, transport, and processing, various dried sample devices and methods have emerged. In dried sample devices, a biological sample is collected in the form of a drop or two of fluid such as whole blood. The blood is collected on filter paper and allowed to dry prior to leaving the collection facility. One benefit of using dried blood samples is that dried blood samples are not classified as a special shipping required biohazard material and may be transported through the mail system or other common delivery service just as any other package.

Additionally, even when a blood or other fluid sample is removed from the body, the concentration of various components within the sample can change over time due to various ongoing reactions. For example, biochemical and cellular changes, such as red blood cells metabolizing plasma glucose for continued cellular respiration, continue in liquid samples. Additionally, when using dried whole blood collection methods, such as collection on Whatman 903 filter paper, as the blood dries, the red cells hemolyze which then becomes mixed with red blood cell membrane cholesterol. The red blood cell membrane cholesterol, which is not normally in the serum portion of the blood, then becomes mixed in with serum cholesterol. Such a mixing may yield a clinically significant increase in a patient cholesterol result. Dried fluid samples have the advantage of reducing various reactions, thereby preserving certain components for later analysis.

The transportation and handling of dried fluid samples is thus a significant improvement over transportation and handling of liquid samples. Merely drying a fluid sample does not always ensure the usefulness of the sample. By way of example, in order to perform analysis of certain dissolved blood components a whole blood sample cannot be used. For example, hemoglobin can interfere with serum analytes at the light absorbance in the instrumental step of clinical analyte testing. Accordingly, the red blood cells must first be separated from the blood plasma or serum prior to drying. The most conventional manner of separating serum or plasma from blood cells is by centrifugation. Centrifugation, of course, requires more than a few drops of blood. Additionally, expensive and space consuming equipment must be maintained at the collection site to perform centrifugation.

Various approaches have been developed to provide for separation of blood samples prior to drying of the samples. For example, U.S. Pat. No. 5,064,541, issued to Jeng et al. on Nov. 12, 1991, describes a device which separates plasma from red blood cells that uses an agglutination agent in a filter to clump red blood cells together. The incorporation of an additional biochemical filter in the device adds to the complexity and cost of the device. Additionally, the amount of blood collected may overwhelm the ability of the red blood cell agglutinating agent to work on all of the red blood cells applied in the whole blood sample.

U.S. Pat. No. 4,816,224, issued to Vogel, et al. on Mar. 28, 1989, describes a series of wicking papers and a relative large sample holder with different embodiments that contain many different components. The device is complex and requires significant foot print space when shipping or undergoing sample extraction at a remote laboratory.

U.S. Pat. No. 6,258,045, issued to Ray et al. on Jul. 10, 2001, describes a device which requires tubing for capillary collection of whole blood along with filtration and multiple layers of reactive or non-reactive materials for plasma separation and testing. Capillary collection tubes require a certain level of operator experience and inflict additional pain on the patient when compared to a simple lancet stick. Additionally, the glass tube can be broken or become detached.

Traditional devices for obtaining dried fluid samples further incorporate indirect methods for ensuring that the proper amount of fluid has been collected to allow the desired separation. Some devices incorporate an indicator which changes color or a portion of the strip which provides a chemical reaction. Such devices do not provide an indication of whether or not too large a sample of fluid has been collected.

Therefore, a collecting device that is self-contained and can be used to provide stable dried biological components to a laboratory would be beneficial. Further benefits would be realized if the device is simple to manufacture and provides accurate results. Further benefits would be provided by a device which enables both the sample collector and laboratory personal to visually directly observe the amount of fluids, such as serum or plasma or red blood cells, which have been collected. A device that can be used to separate fluids such as blood into separate components and which is easy to mail without additional charges would also be beneficial.

SUMMARY

The present invention is directed to a device for separating and drying a fluid sample. In one embodiment, a fluid sample collection card assembly in one embodiment includes a case including a tray assembly receiving cavity accessible through a mouth portion of the case, and a tray assembly, the tray assembly including an absorbent layer supported by a base portion, the base portion including (i) a tray portion configured to be removably received within the tray assembly receiving cavity and (ii) a faceplate portion configured to at least substantially close the mouth when the tray portion is received within the tray assembly receiving cavity.

These and other advantages and features of the present invention may be discerned from reviewing the accompanying drawings and the detailed description of the preferred embodiment of the invention.

BRIEF DESCRIPTION OF THE DRAWINGS

The present invention may take form in various system and method components and arrangement of system and method components. The drawings are only for purposes of illustrating exemplary embodiments and are not to be construed as limiting the invention.

DESCRIPTION

Figure 1:
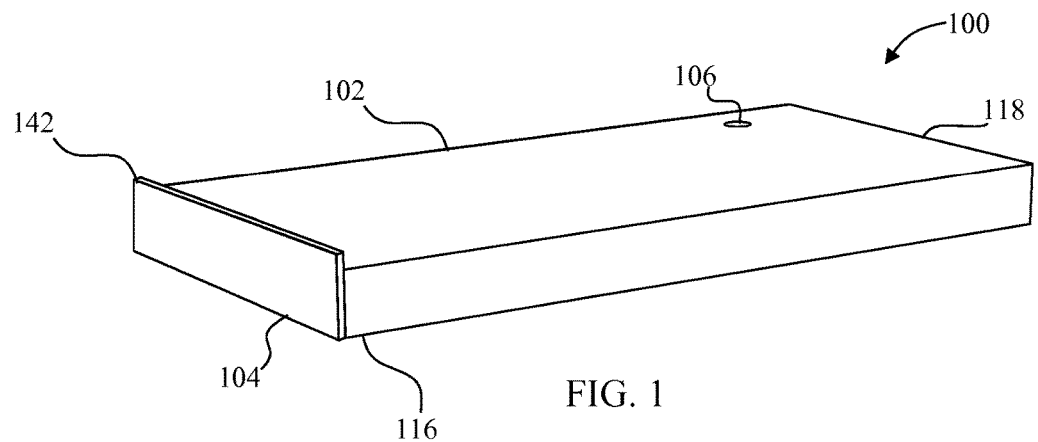
FIG. 1 depicts a top perspective view of a separator card assembly including a tray assembly with a sample receiving portion of an absorbent layer accessible through a sample window and a sample indicating portion of the absorbent layer viewable through a viewing window in accordance with principles of the invention.

Referring to FIG. 1, a fluid separator card assembly 100 is shown which in this embodiment is configured to separate serum and plasma in a blood sample. The fluid separator card assembly 100 includes a case 102 and a tray assembly 104. In one embodiment, the case 102 has a depth (from the upper surface to the lower surface as depicted in FIG. 1) of about ¼ inch or less, preferably about ⅜ inch. The case 102, also shown in FIG. 2, includes a ventilation hole 106 and a ventilation hole 108. Two pair of rails 110 and 112 are located on opposite sides of the case 102. The rail pairs 110 and 112 extend from a mouth 114 at a forward end portion 116 of the case 102 to a rear end portion 118 of the case which in this embodiment is sealed. The rail pairs 110 and 112 define a pair of opposed grooves 120 and 122, respectively. The mouth 114 provides access to a tray assembly receiving cavity 124 in which the rail pairs 110 and 112 and opposed grooves 120 and 122 are located.

Figure 3:
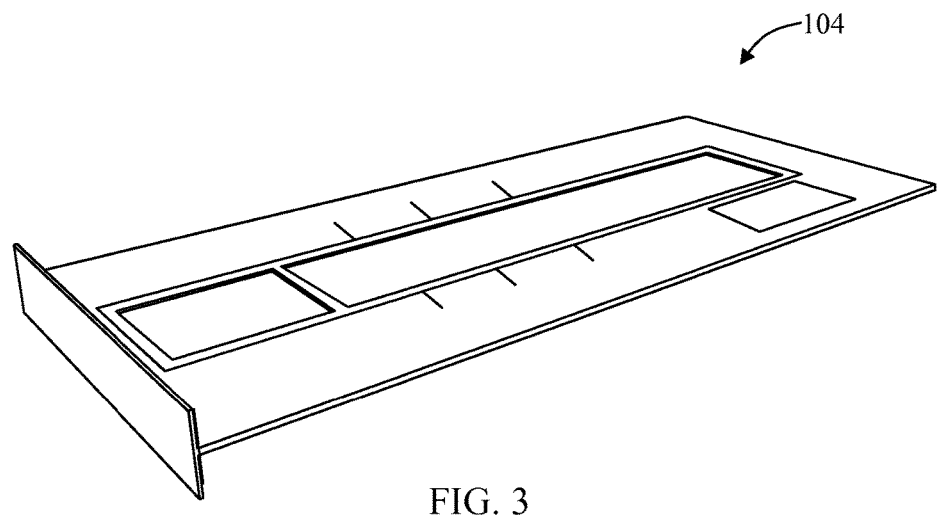
FIG. 3 depicts a perspective view of the tray assembly of FIG. 1 showing reference marks on an upper surface of a tray portion and a sample receiving portion of the absorbent layer accessible through a sample window portion of an insert and a sample portion of the absorbent layer viewable through a sample viewing portion of the insert.
Figure 4:
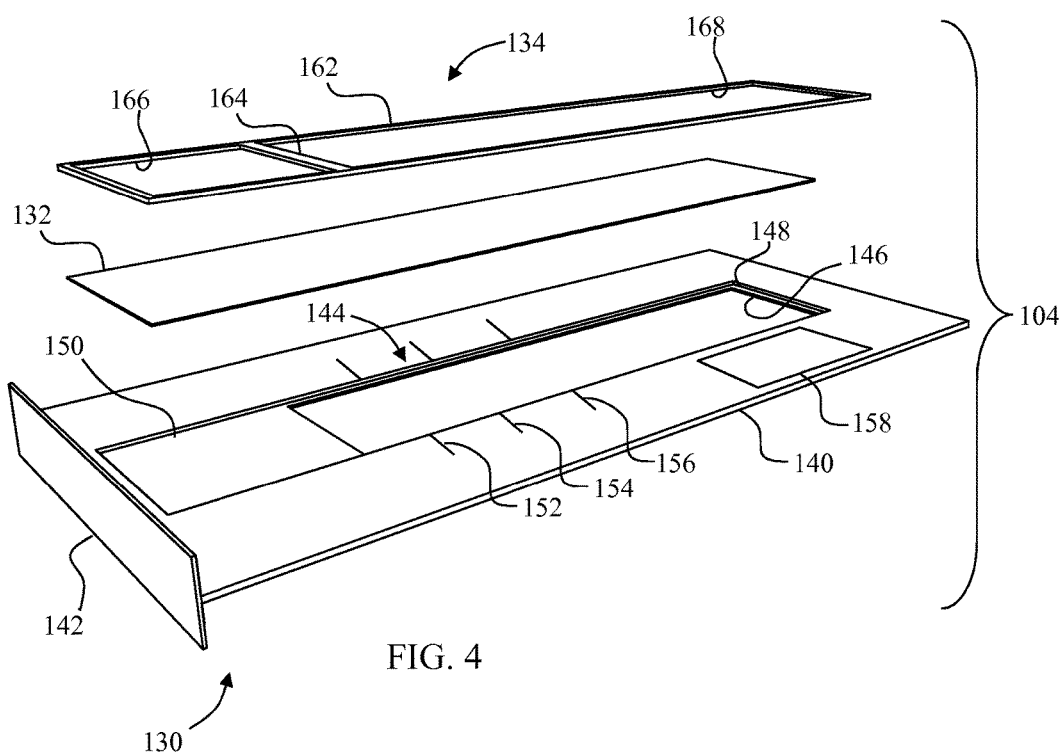
FIG. 4 depicts an exploded perspective view of the tray assembly of FIG. 3.
Figure 5:
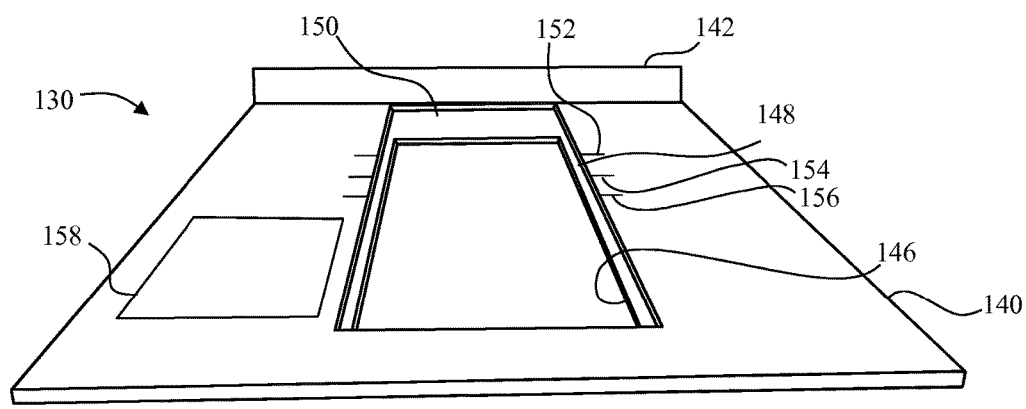
FIG. 5 depicts a top, rear perspective view of the tray portion of the tray assembly of FIG. 3.

The opposed grooves 120 and 122 are sized and positioned to receive the tray assembly 104 shown in further detail in FIGS. 3 and 4. The tray assembly 104 includes a base portion 130, an absorbent layer 132, and an insert 134. The base portion 130 includes a tray portion 140 and a faceplate 142. A holder portion 144 in the tray portion 140 includes an opening 146 which is surrounded by a lip 148. The lip 148 includes a non-absorbent ledge 150.

In the embodiment of FIGS. 1-5, a series of reference marks 152, 154, and 156, which extend outwardly from the sides of the holder portion, along with an identification block 158 are provided. Alternatively, the reference marks 152, 154, and 156 and/or the identification block 158 are provided on the insert 134. In some embodiments, either the reference marks 152, 154, and 156 and/or the identification block 158 is omitted. In other embodiments, more or fewer reference marks 152, 154, and 156 are provided. Instructions for using the separator card assembly 100 may be printed in the identification block 158 and space for insertion of patient identification data may also be provided therein.

The insert 134 includes an outer frame portion 162 and a bridge 164 which extends between opposite sides of the frame portion 162. The frame portion 162 and the bridge 164 define a sample window 166 and a viewing window 168. The insert 134 in some embodiments is formed from a polymer or other nonabsorbent material.

The tray portion 140 in one embodiment is fabricated from a polymer or other nonabsorbent material. In some embodiments, the ledge 150 includes a well or depression (not shown) into which excess fluid sample pools until absorbed by the absorbent layer 132. In other embodiments, the ledge 150 is omitted and the opening 146 extends to a location adjacent to the faceplate 142.

In some embodiments, including embodiments wherein the ledge 150 is constructed of an absorbent material, a non-absorbent material is used to line the ledge 150. The non-absorbent material in some embodiments is Mylar, which is used for its imperviousness to liquid penetration. Other materials which may be used to form an acceptable liquid barrier include thin sheets of Polyethylene, porous UHMWPE film, FEP film, polyester treated sheeting and polypropylene.

Another material which provides an acceptable liquid barrier is porous ePTF film, commercially available from DeWal Industries, Inc. of Saunderstown, R.I. as product number D/W 233MS. The ePTF material is a fluoropolymer material which contains a fluorocarbon material at its surface. The fluorine molecule is the most electronegative element, thereby providing a desired hydrophobic quality. Specifically, it is believed that the fluorocarbon additive to the base plastic polymer in this material and other fluoropolymers enhances the separation of plasma from the red blood cells in the touching absorbent layer 132.

The tray assembly 104 is assembled by inserting the absorbent layer 132 into the holder portion 144 of the base portion 130 on top of the lip 148 (see FIG. 4). The absorbent layer 132 is sized to contact the lip 148 on all sides of the opening 146. Preferably, the absorbent layer 132 does not extend up the wall extending from the lip 148 to the upper surface of the tray portion 140. The absorbent layer 132 in this embodiment is made from Whatman LF-1 material, commercially available from Whatman Inc. of Florham Park, N.J. Other suitable material may be used, such as, but not limited to, porous materials that allow liquid and suspended solids to differentially flow and separate based on the molecular size of the molecules.

Additionally, the characteristics of the absorbent layer 132 may be modified by incorporating designs that utilize other physical forces that affect the flow of substances through the absorbent layer 132. Such physical forces include hydrophobic or hydrophilic interactions as well as ionic interactions. Additionally, temporary hydrogen bonding interactions and gravitational effects may be used to augment or retard flow to provide the desired separation or alteration of a separation of the flowing liquids and suspended cells or other solid materials.

The insert 134 is then positioned within the holder portion 144 on top of the absorbent layer 132. The insert 134 is sized to be at least slightly longer and wider than the holder portion 140. Accordingly, as the insert 134 is positioned within the holder portion 140, the insert 134 frictionally engages the walls of the holder portion 144 trapping the absorbent layer against the lip 148. As shown most clearly in FIG. 4, the ledge 150 is substantially coextensive with the sample window 166 when the ledge 150 and the sample window 166 are projected onto a plane defined by the tray portion 140.

Amongst other functions, the bridge 164 provides additional stiffness, thereby providing for increased friction. Accordingly, in some embodiments, additional bridges are provided to provide additional stiffness. In some embodiments, the bridges are used in place of the reference marks 152, 154, and 156.

In some embodiments, the bridge 164 is omitted. For example, the bridge 164 may be omitted in embodiments where the material used to construct the insert 134 is sufficiently stiff to provide the desired friction al hold or in embodiments where the insert 134 is sonically welded or otherwise attached to the holder portion 144.

Once the absorbent layer 132 is secured on the tray portion 140, the tray assembly 104 is positioned in the case 102 by aligning the tray portion 140 with the grooves 120/122. The tray assembly 104 is then pushed through the mouth 114 and into the tray assembly receiving cavity 124 until the faceplate 142 substantially closes the mouth 114.

In some embodiments, a small stand-off is established between the faceplate 142 and the case 102 to provide for ventilation of the tray assembly receiving cavity 124. The standoff may be accomplished by providing a protuberance on either the case 102 or the faceplate 142. In the embodiment of FIG. 1, the faceplate 142 contacts the case 102. In some embodiments, a latch or other configuration is provided to removably secure the tray assembly 104 within the case 102. By way of example, the tray portion 140 in some embodiments is provided with a protuberance (not shown) which engages a hollowed portion of one of the rails 110/112.

The assembled separator card assembly 100 may be further packaged for storage until a fluid sample is needed. A fluid sample may be obtained in a clinical or laboratory setting. Alternatively, the separator card 100 may be used by lay persons at virtually any location. When a sample is to be collected, a user at least partially removes the tray assembly 104 from the case 102. Removal of the tray assembly 104 is facilitated in the embodiment of FIG. 1 in that a portion of the faceplate 142 extends above the upper surface of the case 102 as shown in FIG. 1. In other embodiments, a tab is provided. Accordingly, a user pushes against the faceplate 142 to force the tray assembly 104 away from the case 102.

The tray assembly 104 is moved outwardly at least until the sample window 166 is exposed. A sample is obtained by producing the fluid, such as by pricking a finger to obtain blood. Four to five drops of blood or other fluid is then dripped onto the absorbent layer 132 through the sample window 166 such that the fluid sample contacts the absorbent layer 132. In embodiments which do not include a bridge 164 defining a sample receiving portion of the absorbent layer 132, the sample receiving portion of the absorbent layer 132 is indicated in another manner such as by marking on the absorbent layer 132 or by a mark on the insert 134 or upper surface of the tray portion 140.

When the fluid sample contacts the absorbent layer 132, the sample is wicked by the absorbent layer 132, and preferentially aided in movement and separation by the chemical or physical nature of the ledge 150, into the portion of the absorbent layer 132 viewable through the viewing window 168. As additional fluid is placed into the portion of the absorbent layer 132 accessible through the sample window 166, the wicked fluid will become visible through the viewing window 168.

In embodiments simply requiring 4 to 5 drops of blood, the reference marks 152, 154, and 156 may be omitted, and collection of fluid terminated once the requisite number of drops has been provided. In other embodiments, the reference marks 152, 154, and 156 are used to indicate when a sufficient amount of fluid has been provided.

Specifically, once the fluid reaches the reference line 152 as fluid is continuing to be provided to the sample portion of the absorbent layer 132, sufficient fluid has been absorbed to perform a single test on the separated portion of the fluid. Thus, in the case of blood, plasma will be wicked along the absorbent layer 132. When the plasma reaches the reference line 152, provision of blood is terminated if a single test is to be performed. The plasma will continue to wick beyond the reference line, thereby providing sufficient plasma for conducting a single test.

The reference lines 154 and 156 may be provided to indicate when sufficient blood or other fluid has been absorbed to separate a quantity of plasma or other fluid component necessary for performance of two tests and three tests, respectively.

The amount of fluid that is necessary to obtain the desired amount of fluid component will vary based not only on the materials used, but also based upon the geometry of the channel formed. By way of example, using materials identified above absorbent layers may be formed with a width of from about 0.6 centimeters to about 4 centimeters when separating plasma from a blood sample. Optimum separation of plasma, however, is obtained with a width of about 1 centimeter. By optimizing the separation of the plasma, less blood is needed to obtain a particular amount of plasma.

The length of the absorbent layer 132 is also a consideration in ensuring sufficient separation of a sample fluid. By way of example, as the volume of sample fluid deposited in the absorbent layer 132 increases, the red blood cells, in the case of blood, will travel further along the absorbent layer 132. Thus, to ensure that a sufficient separation of a sample fluid occurs in the event too much sample is provided, the length of the absorbent layer 132 may be increased.

Figure 2:
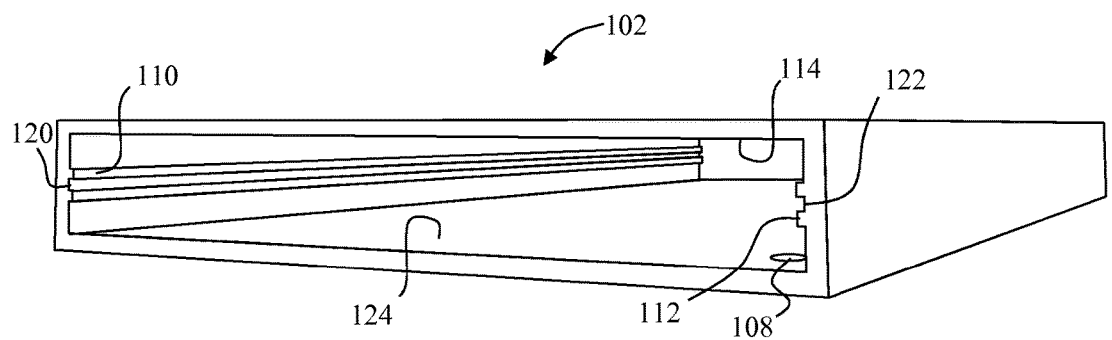
FIG. 2 depicts a perspective view of the case of FIG. 1.

Once the desired sample has been collected, the absorbent layer 132 is left to dry. If desired, the tray assembly 104 may be reinserted into the case 102 in the manner described above while the absorbent layer 132 is still damp. The ventilation holes 106/108 which extend from the tray assembly receiving cavity 124 to the atmosphere outside of the case 102 assist with drying. Preferably the ventilation holes 106/108 are positioned such that if an object is inserted through the ventilation holes 106/108, the object will contact the tray portion 140 and not the absorbent layer 132. For example, as depicted in FIGS. 1 and 2, the ventilation holes 106/108 are located at the outer edges of the case. In some embodiments, the ventilation holes 106/108 are sized such that liquids will not readily be passed through the ventilation holes 106/108 to further protect the obtained sample from contamination.

Figure 6:
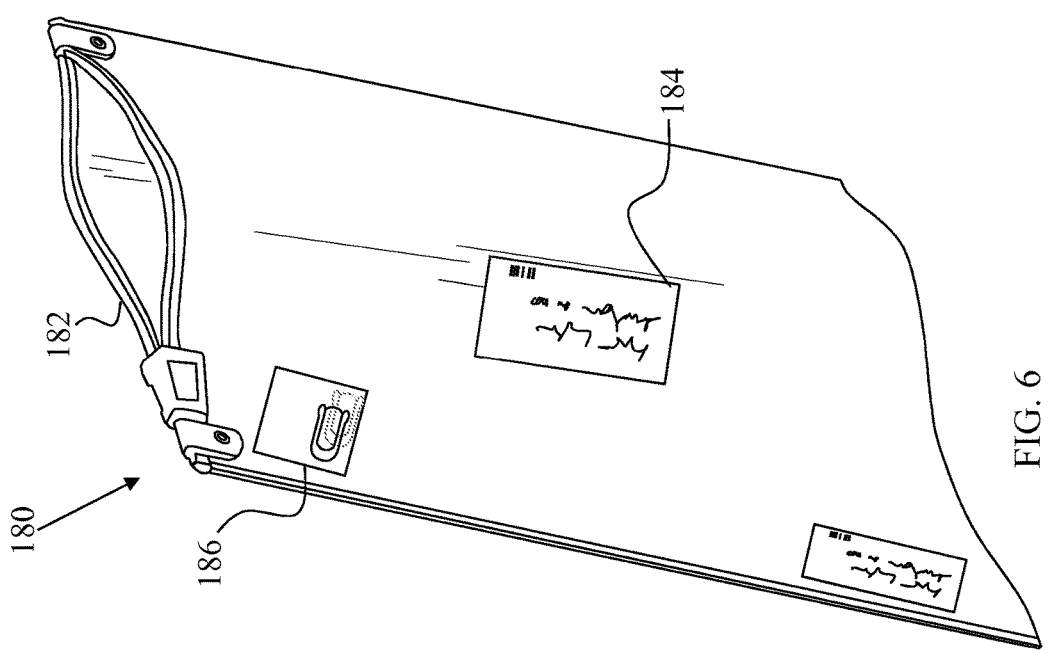
FIG. 6 depicts a perspective view of a resealable packet that may be used to transfer the separator card assembly of FIG. 1 through a carrier service to a laboratory or other facility.

The separator card assembly 100 may then be shipped via any desired mode of transportation to a processing facility. The dried fluid sample contained in the absorbent layer 132 may be stored for a relatively long time without undue degradation of the sample. Nonetheless, the shelf life of the sample may be extended by placement of the separator card assembly 100 in a storage container such as the package 180 shown in FIG. 6.

The package 180 is a gas impermeable package such as a plastic or foil package. The package 180 includes a resealable opening 182. The resealable opening 182 may include a tamper proof mechanism to provide an indication that the package 180 has been opened after a sample has been sealed therein. The package 180 is sized to accept the separator card assembly 100 therein, and may be further dimensioned to allow for insertion into a flat envelope of standard size for automated processing by a postal facility. Alternatively, the package 180 may include a preprinted address 184 and prepaid postage 186 as in the embodiment of FIG. 6.

In one embodiment, an oxygen scrubber (not shown) is provided with the package 180. An oxygen scrubber typically includes thin shavings including pieces of metal and a carrier desiccant that loosely holds some amount of water. When the package 180 is sealed with an oxygen scrubber therein, oxygen present within the package 180 reacts with the metal in the presence of water to form rust, thereby binding the oxygen. Elimination of oxygen from the atmosphere of the package 180 provides increased stability for various components within the dried fluid sample. For example, lipid analytes such as HDL, cholesterol, and triglycerides may be further stabilized by removal of oxygen from the atmosphere in which the sample is stored.

If desired, the separator card assembly 100 may be placed within the package 180 and the package 180 sealed before a fluid sample within the absorbent layer 132 has been dried. Sealing the package 180 with a wet fluid sample held in the separator card assembly 100 inhibits drying of the sample.

Figure 7:
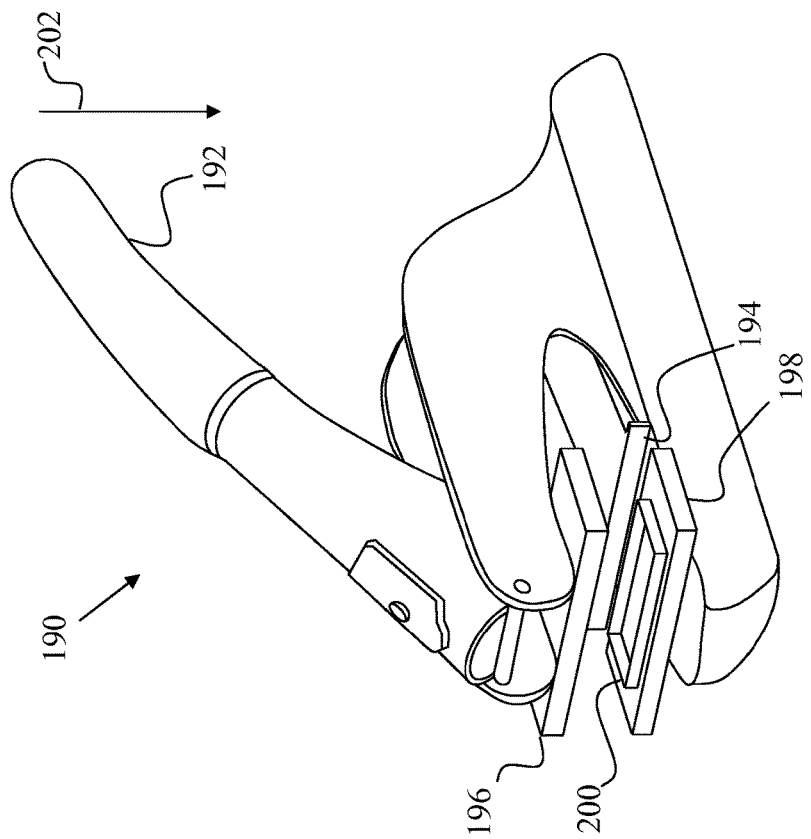
FIG. 7 depicts a perspective view of a removal tool that may be used to separate at least a portion of the absorbent strip of the separator card assembly of FIG. 1.

Removal of at least a portion of the absorbent layer 132 from the tray assembly 104 for further processing is facilitated by the opening 146. One device that may be used to remove at least a portion of the absorbent layer 132 is the removal tool 190 shown in FIG. 7. The removal tool 190 includes a lever arm 192, a guide stop 194, an upper mandrel 196 and a lower mandrel 198. The lower mandrel 198 includes a shaped cutting edge 200 which is sized to fit inside both the viewing window 168 and the opening 146. The upper mandrel 196 includes a protuberance (not shown) that is slightly smaller than the viewing window 168 and the opening 146 and positioned to fit within the shaped cutting edge 200.

Accordingly, removal of the portion of the absorbent layer 132 including the separated sample is accomplished by removing the tray assembly 104 from the case 102 as described above and placing the tray assembly 104 on the removal tool 190. Correct placement of the tray assembly 104 on the removal tool 190 may be guided by the guide stop 194. Alternatively, the viewing window 168 and opening 146 are simply positioned over the shaped cutting edge 200. Thereafter, movement of the lever arm 192 in the direction of the arrow 202 forces the protuberance (not shown) on the upper mandrel 196 against the absorbent layer 132 at a location aligned with the viewing window 168 and opening 146. The portion of the absorbent layer 132 viewable through the viewing window 168 is thus forced against the shaped cutting edge 200 which separates the portion of the absorbent layer 132 including the separated sample from the tray assembly 104.

Various other modifications of the separator card assembly 100 may be incorporated to optimize the separator card for particular tests. In one embodiment, polyhexamethylene biguanide hydrochloride (PHMB) is incorporated into the absorbent layer 104. PHMB is an additive used in bandages for inhibiting the growth of microbial organisms such as bacteria and fungi.

In a further embodiment, prior to blood or other biological fluid application, a polypeptide fraction of highly purified dermal collagen of porcine origin (Prionex from Pentapharm) is applied and dried to the separator card absorbent layer 104. A separator card 100 treated with Prionex applied to the absorbent layer 104 at a 0.1 percent concentration can yield close to double the separation area of serum or plasma for a given volume of blood applied to the absorbent layer 104. Other substances such as various proteins, detergents, salts or solvents, or other chemicals may also be used to enhance separation of a sample fluid.

Another additive that is useful when obtaining fluid samples in the form of blood is sucrose. In particular, cholesterol containing molecules and cholesterol itself are hydrophobic molecules which in pure form do not mix with an aqueous solution. The complex arrangement of proteins, salts and carbohydrate and complex carbohydrate in blood, however, holds these hydrophobic molecules in suspension. Disruption of these serum components during drying could result in clumping or aggregation of the hydrophobic molecules rendering successful hydration of the hydrophobic molecules problematic.

Application of sucrose in 1 to 10% wt./vol. concentration followed by drying to the absorbent layer 104, however, provides a more reproducible drying and rehydration of cholesterol containing molecules such as HDL, LDL and the cholesterol molecule itself. It is believed that the carbohydrate sucrose molecules are surrounded by water molecules when a fluid sample is added. Thus, the sucrose layers surround the hydrophobic cholesterol or triglyceride molecules during the drying and inhibit aggregation via hydrophobic binding of the sucrose shielded hydrophobic molecules.

While the present invention has been illustrated by the description of exemplary processes and system components, and while the various processes and components have been described in considerable detail, applicant does not intend to restrict or in any limit the scope of the appended claims to such detail. Additional advantages and modifications will also readily appear to those skilled in the art. The invention in its broadest aspects is therefore not limited to the specific details, implementations, or illustrative examples shown and described. Accordingly, departures may be made from such details without departing from the spirit or scope of applicant's general inventive concept.

The invention claimed is:

1. A fluid sample collection card assembly comprising:
a case including a tray assembly receiving cavity accessible through a mouth portion of the case; and a tray assembly, the tray assembly including an absorbent layer supported by a base portion, the base portion including (i) a tray portion configured to be removably received within the tray assembly receiving cavity and (ii) a faceplate portion configured to at least substantially close the mouth when the tray portion is received within the tray assembly receiving cavity, wherein the faceplate portion is configured to abut the case when the tray portion is received within the tray assembly receiving cavity.

2. A fluid sample collection card assembly comprising:
a case including a tray assembly receiving cavity accessible through a mouth portion of the case; and a tray assembly, the tray assembly including an absorbent layer supported by a base portion, the base portion including (i) a tray portion configured to be removably received within the tray assembly receiving cavity and (ii) a faceplate portion configured to at least substantially close the mouth when the tray portion is received within the tray assembly receiving cavity, wherein: the tray portion defines a holder portion located beneath an upper surface of the tray portion; and the absorbent layer is positioned on an upper surface of the holder portion.

3. The assembly of claim 2, tray assembly further comprising:
an insert securing the absorbent layer to the upper surface of the holder portion.

4. The assembly of claim 3, wherein: the holder has a first length and a first width; the insert has a second length and a second width; and at least one of the second length and the second width is greater than the first length and the first width, respectively, such that the insert is frictionally engaged with the holder.

5. The assembly of claim 3, insert further comprising:
a bridge extending from a first side of the insert to a second side of the insert.

6. The assembly of claim 5, wherein the bridge defines a portion of a sample window and a portion of a viewing window.

7. The assembly of claim 6, tray assembly further comprising: a lip portion in the holder portion defining an opening in the base portion.

8. The assembly of claim 7, wherein:
the lip portion includes a ledge which is substantially coextensive with the sample window when the ledge and the sample window are projected onto a plane defined by the tray portion.

9. The assembly of claim 8, wherein the ledge defines a well portion.

10. The assembly of claim 3, tray assembly further comprising: a lip portion in the holder portion defining an opening in the base portion.

11. The assembly of claim 3, wherein the case comprises:
at least one ventilation hole extending from the tray assembly receiving cavity to an outer surface of the case.

12. The assembly of claim 3, wherein the case comprises:
at least one pair of rails extending along the tray assembly receiving cavity, the at least one pair of rails defining a groove configured to receive a portion of the tray portion therein.

13. The assembly of claim 9, wherein the faceplate portion is configured to abut the case when the tray portion is received within the tray assembly receiving cavity.

* * * * *